United States Patent
Han et al.

(10) Patent No.: US 11,952,357 B2
(45) Date of Patent: *Apr. 9, 2024

(54) EPOXIDE WITH LOW TOTAL CHLORINE CONTENT AND NO HEAVY METAL RESIDUES AND PREPARATION METHOD THEREOF

(71) Applicant: JIANGSU TETRA NEW MATERIAL TECHNOLOGY CO., LTD., Taizhou (CN)

(72) Inventors: Jianwei Han, Taizhou (CN); Quan Jia, Taizhou (CN); Yangjun Chang, Taizhou (CN); Xiangming Cao, Taizhou (CN)

(73) Assignee: JIANGSU TETRA NEW MATERIAL TECHNOLOGY CO., LTD., Taizhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/761,501

(22) PCT Filed: Sep. 17, 2020

(86) PCT No.: PCT/CN2020/115790
§ 371 (c)(1),
(2) Date: Mar. 17, 2022

(87) PCT Pub. No.: WO2021/052400
PCT Pub. Date: Mar. 25, 2021

(65) Prior Publication Data
US 2022/0363653 A1    Nov. 17, 2022

(30) Foreign Application Priority Data
Sep. 17, 2019  (CN) .......................... 201910875227.3

(51) Int. Cl.
*C07D 301/16* (2006.01)
*C07D 303/44* (2006.01)

(52) U.S. Cl.
CPC ......... *C07D 301/16* (2013.01); *C07D 303/44* (2013.01)

(58) Field of Classification Search
CPC ........................... C07D 303/44; C07D 301/16
See application file for complete search history.

(56) References Cited

U.S. PATENT DOCUMENTS

2012/0029217 A1* 2/2012 Nagato ................ C07D 303/40
549/523
2023/0212133 A1* 7/2023 Han ..................... C07D 303/04
549/531

FOREIGN PATENT DOCUMENTS

| CN | 102391211 A | 3/2012 |
| CN | 110183401 A | 8/2019 |
| CN | 110591054 A | 12/2019 |

OTHER PUBLICATIONS

Machine translation of JP2010155805A, Hiroshi et al., Method for producing epoxy compound, Jul. 15, 2010, p. 1-7 (Year: 2010).*
Office Action issued in corresponding Chinese Patent Application No. 201910875227.3, dated Feb. 3, 2021, 11 pages (with English translation).
International Search Report and Written Opinion issued in corresponding International Patent Application No. PCT/ CN2020/ 115790, dated Dec. 23, 2020, 7 pages (English translation only).

* cited by examiner

*Primary Examiner* — Samantha L Shterengarts
*Assistant Examiner* — Karen Cheng
(74) *Attorney, Agent, or Firm* — Day Pitney LLP; Anthony A. Kassas

(57) ABSTRACT

The present disclosure relates to the field of epoxide resin, and more particularly to an epoxide with a low total chlorine content and no heavy metal residues, and a preparation method thereof. Disclosed is an epoxide prepared from raw materials including an unsaturated cycloaliphatic compound containing a double bond, hydrogen peroxide, an organic acid compound, a solvent and an alkaline salt; wherein a molar ratio of the organic acid compound to the unsaturated cycloaliphatic compound containing a double bond is (1-1.5):1. The obtained epoxides obtained in the present disclosure have a high purity, a high yield, a low solvent content, low chroma, and a low chlorine and metal ion content; the reaction system is simple, environmentally friendly, safe and controllable, and the production cost is low, which can meet the technical and economic requirements and are suitable for large-scale industrial production.

8 Claims, No Drawings

EPOXIDE WITH LOW TOTAL CHLORINE CONTENT AND NO HEAVY METAL RESIDUES AND PREPARATION METHOD THEREOF

CROSS REFERENCE TO RELATED APPLICATION

This application is a U.S. national stage application under 35 U.S.C. 371 of co-pending International Application No. PCT/CN2020/115790 filed on Sep. 17, 2020, which in turn claims the benefit and priority of Chinese Patent Application No. 201910875227.3, entitled "Epoxide with Low Total Chlorine Content and No Heavy Metal Residues and Preparation Method thereof" filed on Sep. 17, 2019, the contents of which is incorporated by reference herein in its entirety for any purpose whatsoever.

TECHNICAL FIELD

The present disclosure relates to the field of epoxide resin, and more particularly to an epoxide with a low total chlorine content and no heavy metal residues, and a preparation method thereof.

BACKGROUND ART

Cycloaliphatic epoxy resins and cured products thereof have been widely used in aerospace, microelectronics packaging, motor insulation and other important industrial fields due to their excellent machinability, thermal stability, electrical insulation and UV radiation resistance, etc. With the increasing performance and functional requirements of polymer materials in modern industry, researches on the synthesis and performance of epoxy resins have been very active in recent years.

Compared with glycidyl ether epoxy resins, cycloaliphatic epoxy resins have the advantages of definite molecular weight and molecular structure, various synthesis methods, strong structural designability, which are easy to change the chemical structure according to actual needs, thereby achieving the adjustment of the physical properties of the resins. Cycloaliphatic epoxy resins are generally liquid with a low viscosity at room temperature before curing, they can often be used directly for construction operations of coatings and electronic packaging materials without solvent dilution, which is convenient for potting, pouring or vacuum injection. The rigid structure of the cycloaliphatic ring and the high crosslinking density of the cured product enable it to have good bonding strength to different substrates, high thermal deformation temperature, excellent chemical resistance, and mechanical and electrical properties. Cycloaliphatic epoxy resins usually do not contain strong ultraviolet chromophores such as aromatic rings. When exposed to high voltage arc, small molecule volatiles such as carbon dioxide, carbon monoxide and water will be produced, and no free carbon will be generated to lead to the formation of conductive pathway, so that they have excellent high voltage leakage resistance. Cycloaliphatic epoxy resins have been widely used in the fields of VLSI packaging, printed circuit board manufacturing, special light-curing coatings, and high-capacity and high-temperature-resistant motor insulation materials for vacuum pressure impregnation technology due to excellent comprehensive properties in recent years.

Since methods for preparing epoxy resins in prior art mostly use traditional catalysts, such catalysts usually contain heavy metal ions (such as tungsten W), so the product also contains a certain amount of heavy metal ion residues; due to the influence of heavy metal ion-containing catalysts, the final product also has heavy metal ion residues, which also affects the curing speed (i.e. gel time) of the product, thereby affecting the cross-linking in the molecule during curing, prolonging the gel time of the product, and affecting the production efficiency and product quality. The cycloaliphatic epoxy resin obtained by the epoxidation of unsaturated cycloaliphatic compounds with organic peroxyacids has a very low content of free chlorine or metal ions, which can be used in places with relatively harsh conditions, and has great advantages.

SUMMARY

In view of some problems existing in the prior art, a first aspect of the present disclosure provides an epoxide prepared from raw materials including an unsaturated cycloaliphatic compound containing a double bond, hydrogen peroxide, an organic acid compound, a solvent and an alkaline salt; wherein a molar ratio of the organic acid compound to the unsaturated cycloaliphatic compound containing a double bond is (1-1.5):1.

In one embodiment of the present disclosure, a weight ratio of the solvent to the unsaturated cycloaliphatic compound containing a double bond is (2.5-4.5):1.

In one embodiment of the present disclosure, the organic acid compound has 3-7 carbon atoms.

In one embodiment of the present disclosure, the organic acid compound is at least one selected from a group consisting of propionic acid, butyric acid, valeric acid, isovaleric acid, acetic anhydride, propionic anhydride, succinic anhydride and maleic anhydride.

In one embodiment of the present disclosure, the unsaturated cycloaliphatic compound containing a double bond is at least one selected from a group consisting of 4-vinylcyclohexene, tetrahydrophthalic acid diglycidyl ester, 3-cyclohexenylmethyl methacrylate, 3-cyclohexenylmethyl acrylate, and poly[(2-vinyl)-1,2-cyclohexanediol]2-ethyl-2-(hydroxymethyl)-1,3-propanediol ether.

In one embodiment of the present disclosure, when the unsaturated cycloaliphatic compound containing a double bond is at least one selected from a group consisting of 4-vinylcyclohexene, tetrahydrophthalic acid diglycidyl ester, 3-cyclohexenylmethyl methacrylate, and 3-cyclohexenylmethyl acrylate, a molar ratio of the hydrogen peroxide to intracyclic double bonds in the unsaturated cycloaliphatic compound containing a double bond is (1-1.7):1.

In one embodiment of the present disclosure, the alkaline salt includes one of sodium carbonate, potassium carbonate and sodium acetate.

In one embodiment of the present disclosure, the solvent includes at least one of an aromatic solvent, a chloralkane solvent, an ester solvent and an alkane solvent.

In one embodiment of the present disclosure, the aromatic solvent includes one of benzene, toluene, ethylbenzene, xylene and trimethylbenzene;

The chloralkane solvent includes one of trichloromethane, dichloroethane, chlorobenzene, 1,3-dichloropropane and 1,2-dichloroethane;

The ester solvent includes one of ethyl acetate, propyl acetate, butyl acetate, propionate, dimethyl carbonate and diethyl carbonate; and The alkane solvent comprises one of a linear alkane, a branched alkane and a cycloalkane hydrocarbon.

In one embodiment of the present disclosure, the solvent further comprises one of methyl isobutyl ketone, methanol, ethanol and tert-butanol.

A second aspect of the present disclosure provides a method for preparing the epoxide comprising the steps of: mixing an unsaturated cycloaliphatic compound containing a double bond, an alkaline salt, and a solvent, and then cooling; adding an organic acid compound thereto; then dropwise adding a hydrogen peroxide solution thereto; standing for layering to obtain an underlayer of an organic phase 1, washing the organic phase 1 with a mixed washing liquid of an inorganic alkaline solution and a reducing salt solution, standing for layering to obtain an underlayer of an organic phase 2, and purifying the organic phase 2 to obtain the epoxide.

In one embodiment of the present disclosure, a weight ratio of the mixed washing liquid to the solvent is 1:(2.5-3.5).

In one embodiment of the present disclosure, a time for dropwise adding the hydrogen peroxide solution is 1-3 h.

In one embodiment of the present disclosure, the inorganic alkaline in the inorganic alkaline solution includes one of sodium hydroxide, potassium hydroxide, sodium carbonate, potassium carbonate, sodium bicarbonate, potassium hydroxide and ammonium hydroxide;

A concentration of the inorganic alkaline solution is 20-40 wt %.

In one embodiment of the present disclosure, the reducing salt in the reducing salt solution includes one of sodium sulfite, ferrous chloride, sodium thiosulfate and ferrous sulfate;

A concentration of the reducing salt solution is 10-20 wt %.

In one embodiment of the present disclosure, the reducing salt solution accounts for 40-45 wt % of the mixed washing liquid.

In one embodiment of the present disclosure, the organic phase 2 was further washed with an aqueous solution.

In one embodiment of the present disclosure, the aqueous solution contains a small-molecule amine and trehalose;

A total amount of the small-molecular amine and trehalose preferably accounts for 15-30 wt % of the aqueous solution;

A weight ratio of the small-molecular amine to trehalose is (3-5):1.

In one embodiment of the present disclosure, a weight ratio of the aqueous solution to the solvent is 1:(2.5-3.5).

In one embodiment of the present disclosure, the purifying includes a vacuum distillation and a two-stage thin film distillation.

In one embodiment of the present disclosure, the two-stage thin film distillation includes a first-stage thin film distillation and a second-stage thin film distillation performed in sequence; a temperature of the first-stage thin film distillation is 30-90° C., and a pressure is 200-250 Pa; a temperature of the second-stage thin film distillation is 75-130° C., and a pressure is 20-40 Pa.

Compared with the prior art, the present disclosure has the following beneficial effects:

The obtained epoxides obtained in the present disclosure have a high purity, a high yield, a low solvent content, low chroma, and a low chlorine and metal ion content; the reaction system is simple, environmentally friendly, safe and controllable, and the production cost is low, which can meet the technical and economic requirements and are suitable for large-scale industrial production.

DETAILED DESCRIPTION OF THE EMBODIMENTS

In the first aspect of the present disclosure, an epoxide is provided, which is prepared from raw materials including an unsaturated cycloaliphatic compound containing a double bond, hydrogen peroxide, an organic acid compound, a solvent and an alkaline salt; wherein a molar ratio of the organic acid compound to the unsaturated cycloaliphatic compound containing a double bond is (1-1.5):1.

The raw materials for preparing the epoxides provided by the present disclosure include an unsaturated cycloaliphatic compound containing double bonds.

In the present disclosure, the cycloaliphatic compound is preferably a carbocyclic compound having the general properties of an aliphatic compound and a carbocyclic structure.

In one embodiment, the unsaturated cycloaliphatic compound containing double bonds is preferably at least one selected from the group consisting of 4-vinylcyclohexene, tetrahydrophthalic acid diglycidyl ester, 3-cyclohexene methacrylate methyl ester, 3-cyclohexenylmethyl methacrylate, 3-cyclohexenylmethyl acrylate, and poly[(2-vinyl)-1,2-cyclohexanediol]2-ethyl-2-(hydroxymethyl)-1,3-propanediol ether.

In one embodiment, the poly[(2-vinyl)-1,2-cyclohexanediol]2-ethyl-2-(hydroxymethyl)-1,3-propanediol ether is preferably poly[(2-vinyl)-1,2-cyclohexanediol]2-ethyl-2-(hydroxymethyl)-1,3-propanediol ether (3:1), CAS: 244772-00-7.

The raw materials for preparing the epoxides provided by the present disclosure include hydrogen peroxide.

In one embodiment, when the unsaturated cycloaliphatic compound containing double bonds is at least one selected from a group consisting of 4-vinylcyclohexene, tetrahydrophthalic acid diglycidyl ester, 3-cyclohexenylmethyl methacrylate, and 3-cyclohexenylmethyl acrylate, a molar ratio of the hydrogen peroxide to intracyclic double bonds in the unsaturated cycloaliphatic compound containing double bonds is (1-1.7):1.

In the present disclosure, the intracyclic double bonds refer to double bonds in an alkane ring.

In one embodiment, when the unsaturated cycloaliphatic compound containing double bonds is preferably poly[(2-vinyl)-1,2-cyclohexanediol]2-ethyl-2-(hydroxymethyl) base)-1,3-propanediol ether (3:1), the molar ratio of the hydrogen peroxide to intracyclic double bonds in poly[(2-vinyl)-1,2-cyclohexanediol]2-ethyl-2-(hydroxymethyl) base)-1,3-propanediol ether (3:1) is preferably (1-1.5):1, more preferably 1.2:1.

In one embodiment, the concentration of the hydrogen peroxide solution is preferably 30-50 wt %, more preferably 35 wt %.

The raw materials for preparing the epoxides provided by the present disclosure include an organic acid compound.

In the present disclosure, the organic acid compound is a collective of organic acids and anhydride.

In one embodiment, the organic acid compound preferably has 3-7 carbon atoms; the organic acid compound is preferably selected from at least one of propionic acid, butyric acid, valeric acid, isovaleric acid, acetic anhydride, propionic anhydride, succinic anhydride and maleic anhydride; the organic acid compound is more preferably acetic anhydride; the purity of the acetic anhydride is preferably 98-100 wt %, and there is no restriction on the manufacturers of the acetic anhydride.

It has been experimentally found that the specific contents of hydrogen peroxide, organic acid compounds and unsaturated cycloaliphatic compound containing double bonds are beneficial to improve the purity and colorless transparency of the obtained aliphatic epoxy resin, which may be because when there is too much unsaturated cycloaliphatic compound containing double bonds, they will undergo self-polymerization reaction, thereby reducing the yield of the obtained product; when there is too much hydrogen peroxide in the system, some water will be produced, which will reduce the purity of the system, and also promote the hydrolysis of part of the obtained epoxides, the oxidation of part of the unsaturated cycloaliphatic compounds or the resulting epoxides into ketones, as well as the generation of diepoxides, then various reactions such as decomposition and oxidation in the reaction system are carried out at the same time, which will reduce the yield and make the obtained resin turn yellow, thereby affecting its application in display lamp electronic products; when there is too much organic acid compounds, acid enrichment in the reaction system may be formed, which will promote the decomposition of the obtained epoxy resin, and reduce the yield.

The raw materials for preparing the epoxides provided by the present disclosure include a solvent.

In one embodiment, the weight ratio of the solvent to the unsaturated cycloaliphatic compound containing double bonds is preferably (2.5-4.5):1; more preferably 3:1.

The solvent is preferably at least one of aromatic solvents, chloralkane solvents, ester solvents and alkane solvents.

In one embodiment, the aromatic solvent preferably includes at least one of benzene, toluene, ethylbenzene, xylene and trimethylbenzene; the chloralkane solvent preferably includes at least one of chloroform, dichloroethane, chlorobenzene, 1,3-dichloromethane and 1,2-dichloroethane; the ester solvent preferably includes at least one of ethyl acetate, propyl acetate, butyl acetate, ethyl propionate, dimethyl carbonate and diethyl carbonate; and the alkane solvent preferably includes at least one of straight chain alkanes, branched chain alkanes and cycloalkanes, more preferably n-hexane or cyclohexane.

In one embodiment, the solvent preferably further includes one of methyl isobutyl ketone, methanol, ethanol and tert-butanol.

In one embodiment, the solvent is preferably toluene, and there is no restriction on the manufacturers of the toluene.

The raw materials for preparing the epoxides provided by the present disclosure include an alkaline salt.

In one embodiment, the alkaline salt preferably comprises at least one of sodium carbonate, sodium hydroxide, potassium carbonate, potassium hydroxide and sodium acetate. In one embodiment, the alkaline salt is more preferably sodium acetate, and there is no restriction on the manufacturers of the sodium acetate.

In the present disclosure, the pH value of the reaction system is regulated by neutralizing the acidic substances produced in the reaction process by the alkaline salt, which can avoid the out of control in temperature caused by the acid enrichment in the system, avoid the decomposition of the obtained epoxide, and promote the progress of the oxidation reaction.

The second aspect of the present disclosure provides a method for preparing the epoxide comprising the steps of: mixing an unsaturated cycloaliphatic compound containing double bonds, an alkaline salt, and a solvent, and then cooling; adding an organic acid compound thereto; then dropwise adding a hydrogen peroxide solution thereto; standing for layering to obtain an underlayer of an organic phase 1, washing the organic phase 1 with a mixed washing liquid of an inorganic alkaline solution and a reducing salt solution, standing for layering to obtain an underlayer of an organic phase 2, and purifying the organic phase 2 to obtain the epoxide.

In one embodiment, the method for preparing epoxides at least comprises the steps of:

(1) mixing an unsaturated cycloaliphatic compound containing double bonds, an organic acid compound, an alkaline salt, and a solvent, and cooling;

(2) dropwise adding a hydrogen peroxide solution thereto;

(3) standing for layering to obtain an underlayer of an organic phase 1, washing the organic phase 1 with a washing liquid of an inorganic alkaline solution and a reducing salt solution, and standing for layering to obtain an underlayer of an organic phase 2; and (4) purifying the organic phase 2 to obtain the epoxides.

Step (1),

In one embodiment, a cooling temperature is 5-15° C., preferably 10-15° C.

If the temperature is too low, an initial reaction rate is slow, which is likely to generate the acid accumulation to cause difficulties in controlling the temperature in later stage; if the temperature is too high, it is easy to cause the decomposition of hydrogen peroxide, resulting in an incomplete reaction. The reaction temperature is easy to control and the side reactions are few by cooling the temperature to the above range and dropwise adding hydrogen peroxide; the reaction can be carried out smoothly and gently in a low temperature due to the strong oxidizing property of hydrogen peroxide and exothermic reaction, which can prevent excessive heat release and rapid temperature rise in the early stage of the reaction to cause out of control and production safety risks.

Step (2),

In one embodiment, the process of step (2) is as follows: dropwise adding the hydrogen peroxide solution, and then continuing the reaction for another 2-6 h.

In one embodiment, the time for dropwise adding the hydrogen peroxide solution is preferably 1-3 h, and more preferably 2 h.

In one embodiment, the temperature of the system in step (2) is 15-25° C., and preferably 20° C.

In one embodiment, the pH value of the system in step (2) is 3.0-4.5, and preferably 3.5-4.2.

In the present disclosure, the reaction efficiency can be effectively improved by slowly adding hydrogen peroxide dropwise within 1-3 h and continuing the reaction at 15-25° C. after the completion of dropwise addition, i.e. in a short reaction time, the obtained epoxy resin has a high yield, and the color is colorless and transparent, which may be attributed to the fact that the reaction can be carried out safely, smoothly and efficiently by controlling the system temperature and addition time within the above range; If the temperature is high and the time is short, the reaction will be violent and uncontrollable, and the contact between materials will not be sufficient, which will not only cause the residue and self-polymerization of some diene substances, but also make the produced epoxy resins fully contact with oxidizing substances, promote oxidation, and reduce the yield of the product; If the time is too long, the nucleophilic substances in the system are easy to react with the epoxy resin with large internal tension due to the lack of oxidizing substances in the acid system, thereby promoting the decomposition of the obtained epoxy resin and the generation of by-products, and reducing the yield.

In step (3), allowing the system obtained in step (2) to stand for layering to obtain an underlayer of an organic phase 1, adding a washing liquid of an inorganic alkaline solution and a reducing salt solution thereto, and stirring to wash the organic phase 1 while maintaining a certain pH value; and standing for layering to obtain an underlayer of an organic phase 2.

In one embodiment, the process of step (3) is as follows: standing for layering to obtain an underlayer of an organic phase 1, adding a washing liquid of an inorganic alkaline solution and a reducing salt solution thereto, and stirring to wash the organic phase 1 while maintaining a certain pH value; and standing for layering to obtain an underlayer of an organic phase 2.

In one embodiment, the pH value is preferably 10-12, and more preferably 11.

In one embodiment, the stirring time is preferably 20-40 min, and more preferably 30 min.

In one embodiment, the weight ratio of the washing liquid to the solvent is 1:(1.5-5.5).

In one embodiment, the concentration of the inorganic alkaline solution is preferably 20-40 wt %, more preferably 30 wt %.

In one embodiment, the concentration of the reducing salt solution is preferably 10-20 wt %, more preferably 10 wt %.

In one embodiment, the reducing salt preferably accounts for 40-45 wt % of the washing liquid.

In one embodiment, the inorganic alkali preferably includes one of sodium hydroxide, potassium hydroxide, sodium carbonate, potassium carbonate, sodium bicarbonate, potassium bicarbonate and ammonium hydroxide; more preferably, the inorganic alkaline is sodium hydroxide, and there is no restriction on the manufacturers of the sodium hydroxide.

In one embodiment, the reducing salt preferably includes one of sodium sulfite, ferrous chloride, sodium thiosulfate and ferrous sulfate; more preferably, the reducing salt is sodium sulfite, and there is no restriction on the manufacturers of the sodium sulfite.

It has been experimentally found that washing the obtained reaction solution with an inorganic alkali and a reducing salt at the same time is beneficial to the improvement of the yield of the final product, as well as the formation of colorless and transparent epoxy resin, which may be because the interaction between the reducing salts and the oxidizing substances in the system during stirring can avoid further oxidation of the epoxy resin obtained in the system; In addition, inorganic alkali can neutralize the residual acidic solution in the reaction solution to make it in a free ionic state in the system and transfer from the organic phase to the aqueous phase, and it can also continuously reduce the products of reducing substances and oxidizing substances during the neutralization process, thereby promoting the effect of oxidizing substances and improving the yield of the system.

In the present disclosure, adjusting the content of the reducing salts in the washing liquid can further optimize the yield and chroma of the products, possibly because when there is too much reducing salts, the neutralization of the alkaline solution in the system is saturated, and the reducing salts are easily oxidized to produce acid enrichment, so that some organic acids remain in the organic phase, thereby promoting the decomposition of epoxy resins.

In addition, adjusting the ratio of the washing liquid to the organic solvent can further optimize the yield and chroma of the products, possibly because the small-molecular impurities in the organic phase cannot be completely neutralized and reduced when the content of washing liquid is small, or the small-molecular impurities remain in the organic phase as the saturation is reached; However, when the content of the washing liquid is large, the organic phase tends to shrink inward to form microspheres during stirring due to the large steric hindrance and the hydrophobic ring structure of the epoxy resin, which will affect the free movement of small molecule impurities into the aqueous phase, thereby reducing the chroma of the products.

In one embodiment, the process of step (3) is as follows: standing for layering to obtain an underlayer of an organic phase 1, adding a washing liquid of an inorganic alkaline solution and a reducing salt solution thereto, and stirring to wash the organic phase 1 while maintaining at a certain pH value; standing for layering to obtain an underlayer of an organic phase 2; and then washing with an aqueous solution to obtain an underlayer of an organic phase 3.

In one embodiment, the weight ratio of the aqueous solution to the solvent is preferably 1:(2.5-3.5), more preferably 1:3.

In one embodiment, the aqueous solution preferably contains small-molecular amines and trehalose; the total amount of the small-molecular amines and trehalose preferably accounts for 15-30 wt % of the aqueous solution; more preferably 20 wt %.

In one embodiment, the weight ratio of the small-molecular amines to trehalose is preferably (3-5):1, more preferably 4:1.

In one embodiment, the small-molecular amines are preferably any one of monoethanolamine, diethanolamine, hydroxyethylethylenediamine, and N-acetylethylenediamine; and more preferably N-acetylethylenediamine.

In the present disclosure, washing the product with trehalose and small-molecular amines can further optimize the yield and chroma of the products, possibly because trehalose is a compound with a large molecular weight and is soluble in water, it can interact with the aliphatic segments in the epoxy resin during washing and stirring, so that the relatively concentrated molecular chains in the organic phase are stretched, and the relative freedom of molecules of the small-molecular impurities in the system is improved. On the other hand, the force between trehalose and small-molecule impurities is higher than the force between small molecules and epoxy resins in the process of stirring, so the washing efficiency is improved under the dual action; but the trehalose has a large molecular weight, a low free rotation of chain segments, and a low contact ability with small molecules in the system, while the small-molecule amines are more likely to move between the interface of the aqueous phase and the organic phase under the action of trehalose, thereby bringing out small molecules to interact with trehalose and acting as a bridge; In addition, small-molecule amines can interact with trace metal elements in the system to reduce impurities and optimize chroma; at the same time, in the presence of nucleophilic groups, small-molecular amines can form $N^+$ and further interact with nucleophilic groups, thereby weakening the interaction between nucleophilic groups and epoxy resins, reducing the decomposition of epoxy, and reducing impurities.

In the present disclosure, adjusting the ratio of trehalose to small-molecular amines can further optimize the yield and chroma. It may be because when the content of trehalose is small, the organic phase that shrinks inward as microspheres during stirring has a low degree of extension, and the molecular chain with large steric hindrance forms a diaphragm, which hinders the free movement of small-molecular impurities and small-molecular amines, thereby reducing the removal rate of impurities; when the content of small-molecular amines is small, the bridge effect is low, and the interaction between small-molecular impurities and the aqueous phase is weak, which causes some impurities to remain in the organic phase, thereby reducing the chroma of the product.

In step (4), the present disclosure purifies the underlayer of an organic phase obtained in step (3) to obtain an epoxide.

In one embodiment, the process of step (4) is as follows: first purifying by a vacuum distillation, and then purifying by a two-stage thin film distillation.

In one embodiment, the vacuum degree of the vacuum distillation is preferably −0.05-−0.1 MPa, the temperature is preferably 25-60° C., and the time is preferably 0.5-1 h; more preferably, the vacuum degree of the vacuum distillation is −0.07 MPa, the temperature is preferably 42° C., and the time is 0.75 h.

In one embodiment, the two-stage thin film distillation includes a first-stage thin film distillation and a second-stage thin film distillation performed in sequence; a temperature of the first-stage thin film distillation is 30-90° C., and a pressure is 200-250 Pa; a temperature of the second-stage thin film distillation is 75-130° C., and a pressure is 20-40 Pa.

In one embodiment, the time of the first-stage thin film distillation is preferably 0.5-1.5 h; more preferably 1 h.

In one embodiment, the time of the second-stage thin film distillation is preferably 0.5-2 h.

There is no restriction on the materials of the thin film. In one embodiment of the present disclosure, the thin film is preferably a scraper, and the material is stainless steel 316L.

In the present disclosure, by using a two-stage thin film distillation and controlling the temperature and pressure of the two distillations, the solvent content in the aliphatic epoxy resin can be effectively reduced to less than 0.1%, the purification efficiency of aliphatic epoxy resin can be improved, i.e., the purification can be completed in a short time, and the obtained aliphatic epoxy resin is colorless and transparent. This may be because using a low-temperature high-pressure thin film distillation, followed by a high-temperature low-pressure thin film distillation can effectively reduce the content of solvents, acid substances and other impurities in epoxy resin, and can effectively avoid the occurrence of side reactions during the distillation process, i.e., first using a low-temperature high-pressure thin film distillation can reduce the content of nucleophilic groups with a boiling point lower than the epoxy resin, which can avoid the decomposition of epoxy resins with large internal tension; in the initial distillation stage, the internal friction between the molecular chains is small, the viscosity is low, and the thermal parameters are also low, but the small molecules can move to the surface of the system relatively easily, which can be removed from the system in a short time; however, because the obtained epoxy resin has a certain steric hindrance, the free movement of small molecules is limited, and the solvent content in the obtained epoxy resin is still 1-5%; the solvent in the system can be further reduced after a high-temperature low-pressure thin film distillation, it may be because the molecular chains are entangled together after the previous treatment, the internal friction force in the system is increased, the viscosity is increased, and the thermal parameters are also increased. The free movement of the molecular chains is increased under high temperature and low pressure, so that the internal solvent is further freed to the surface of the system, further removing the participating solvents or small-molecular impurities in the system, and improving the colorless transparency of the epoxy resin.

In the present disclosure, distilling by a one-stage thin film distillation at a higher temperature for 8-15 h, the obtained epoxy resin is pale yellow having a solvent residue of 0.5-1%. This is because the removal of solvent or small molecule impurities on the surface of the system is rapid under high temperature, and the degree of entanglement of molecular chains on the surface of the epoxy resin is high, which hinders the speed and total amount of solvents or other small-molecule impurities in the system to the surface. In addition, side reactions such as decomposition and self-polymerization of the non-uniform epoxy resin will occur under high temperature, which increases the instability of the system, thereby reducing the purity, increasing the solvent content and the degree of color development of the obtained epoxy resin.

Hereinafter, the present disclosure will now be described in further detail by way of examples.

Example 1

In this example, an epoxide was prepared from raw materials including an unsaturated cycloaliphatic compound containing double bonds, hydrogen peroxide, an organic acid compound, a solvent and an alkaline salt.

The unsaturated cycloaliphatic compound containing double bonds was 3-cyclohexenylmethyl methacrylate; the organic acid compound was acetic anhydride with a purity of 98 wt %, and the molar ratio of the acetic anhydride to 3-cyclohexenylmethyl methacrylate was 1.2:1; the concentration of the hydrogen peroxide solution was 35 wt %, the molar ratio of the hydrogen peroxide to the intracyclic double bonds in the 3-cyclohexenylmethyl methacrylate was 1.5:1; the solvent was toluene, and the weight ratio of the toluene to 3-cyclohexenylmethyl methacrylate was 3:1; and the alkaline salt was sodium acetate.

The method for preparing the epoxide comprises the following steps:

(1) The unsaturated cycloaliphatic compound, the organic acid compound, the alkaline salt, and the solvent were mixed, and then cooled to 13° C.;

(2) At a temperature of 20° C. and a pH of 3.7, the hydrogen peroxide solution was added to the above solution dropwise over 2 h, and the reaction was continued for another 4 h;

(3) The resulting solution was left for standing to obtain an underlayer of an organic phase 1, a mixed washing liquid of an inorganic alkaline solution and a reducing salt solution was added thereto and stirred for 20 min at a pH of 11; and the resulting solution was left for standing to obtain an underlayer of an organic phase 2;

(4) The organic phase 2 was first purified by a vacuum distillation at 42° C. for 0.75 h with a vacuum degree of −0.07 MPa, then purified by a two-stage thin film distillation, the temperature of the first-stage thin film distillation was 60° C., the distillation pressure was 200 Pa, the distillation time was 1 h, the temperature of the second-stage thin film distillation was 80° C., the distillation pressure was 20 Pa, and the distillation time was 1 h.

The weight ratio of the mixed washing liquid to the solvent was 1:4.4; the concentration of the inorganic alkaline solution was 30 wt %; the concentration of the reducing salt solution was 10 wt %; the inorganic alkali was sodium hydroxide; the reducing salt was sodium sulfite, and the content of the reducing salt solution was 44 wt % of the mixed washing liquid.

Example 2

In this example, an epoxide was prepared from raw materials including an unsaturated cycloaliphatic compound containing double bonds, hydrogen peroxide, an organic acid compound, a solvent and an alkaline salt.

The unsaturated cycloaliphatic compound containing double bonds was 3-cyclohexenylmethyl acrylate; the organic acid compound was acetic anhydride with a purity of 98 wt %, and the molar ratio of the acetic anhydride to 3-cyclohexenylmethyl acrylate was 1.25:1; the concentration of the hydrogen peroxide solution was 35 wt %, the molar ratio of the hydrogen peroxide to the intracyclic double bonds in the 3-cyclohexenylmethyl acrylate was 1.5:1; the solvent was toluene, and the weight ratio of the toluene to 3-cyclohexenylmethyl acrylate was 3:1; and the alkaline salt was sodium acetate.

The method for preparing the epoxide comprises the following steps:

(1) The unsaturated cycloaliphatic compound, the organic acid compound, the alkaline salt, and the solvent were mixed, and then cooled to 13° C.;

(2) At a temperature of 20° C. and a pH of 3.7, the hydrogen peroxide solution was added to the above solution dropwise over 2 h, and the reaction was continued for another 4 h;

(3) The resulting solution was left for standing to obtain an underlayer of an organic phase 1, a mixed washing liquid of an inorganic alkaline solution and a reducing salt solution was added thereto and stirred for 20 min at a pH of 11; and the resulting solution was left for standing to obtain an underlayer of an organic phase 2;

(4) The organic phase 2 was first purified by a vacuum distillation at 42° C. for 0.75 h with a vacuum degree of −0.07 MPa, then purified by a two-stage thin film distillation, the temperature of the first-stage thin film distillation was 60° C., the distillation pressure was 200 Pa, the distillation time was 1 h, the temperature of the second-stage thin film distillation was 80° C., the distillation pressure was 20 Pa, and the distillation time was 1 h.

The weight ratio of the mixed washing liquid to the solvent was 1:4; the concentration of the inorganic alkaline solution was 30 wt %; the concentration of the reducing salt solution was 10 wt %; the inorganic alkali was sodium hydroxide; the reducing salt was sodium sulfite, and the content of the reducing salt solution was 44 wt % of the mixed washing liquid.

Example 3

In this example, an epoxide was prepared from raw materials including an unsaturated cycloaliphatic compound containing double bonds, hydrogen peroxide, an organic acid compound, a solvent and an alkaline salt.

The unsaturated cycloaliphatic compound containing double bonds was tetrahydrophthalic acid diglycidyl ester; the organic acid compound was acetic anhydride with a purity of 98 wt %, and the molar ratio of the acetic anhydride to tetrahydrophthalic acid diglycidyl ester was 1.4:1; the concentration of the hydrogen peroxide solution was 35 wt %, the molar ratio of the hydrogen peroxide to the intracyclic double bonds in the tetrahydrophthalic acid diglycidyl ester was 1.7:1; the solvent was toluene, and the weight ratio of the toluene to tetrahydrophthalic acid diglycidyl ester was 3:1; and the alkaline salt was sodium acetate.

The method for preparing the epoxide comprises the following steps:

(1) The unsaturated cycloaliphatic compound, the organic acid compound, the alkaline salt, and the solvent were mixed, and then cooled to 13° C.;

(2) At a temperature of 20° C. and a pH of 3.7, the hydrogen peroxide solution was added to the above solution dropwise over 2 h, and the reaction was continued for another 2 h;

(3) The resulting solution was left for standing to obtain an underlayer of an organic phase 1, a mixed washing liquid of an inorganic alkaline solution and a reducing salt solution was added thereto and stirred for 20 min at a pH of 11; and the resulting solution was left for standing to obtain an underlayer of an organic phase 2;

(4) The organic phase 2 was first purified by a vacuum distillation at 42° C. for 0.75 h with a vacuum degree of −0.07 MPa, then purified by a two-stage thin film distillation, the temperature of the first-stage thin film distillation was 70° C., the distillation pressure was 200 Pa, the distillation time was 1 h, the temperature of the second-stage thin film distillation was 100° C., the distillation pressure was 20 Pa, and the distillation time was 1 h.

The weight ratio of the mixed washing liquid to the solvent was 1:5.2; the concentration of the inorganic alkaline solution was 30 wt %; the concentration of the reducing salt solution was 10 wt %; the inorganic alkali was sodium hydroxide; the reducing salt was sodium sulfite, and the content of the reducing salt solution was 41 wt % of the mixed washing liquid.

Example 4

In this example, an epoxide was prepared from raw materials including an unsaturated cycloaliphatic compound containing double bonds, hydrogen peroxide, an organic acid compound, a solvent and an alkaline salt.

The unsaturated cycloaliphatic compound containing double bonds was poly[(2-vinyl)-1,2-cyclohexanediol]2-ethyl-2-(hydroxymethyl)-1,3-propanediol ether (3:1) with a product grade of TTA3150; the organic acid compound was acetic anhydride with a purity of 98 wt %, and the molar ratio of the acetic anhydride to poly[(2-vinyl)-1,2-cyclohexanediol]2-ethyl-2-(hydroxymethyl)-1,3-propanediol ether was 1.4:1; the concentration of the hydrogen peroxide solution was 35 wt %, the molar ratio of the hydrogen peroxide to the intracyclic double bonds in the poly[(2-vinyl)-1,2-cyclohexanediol]2-ethyl-2-(hydroxymethyl)-1,3-propanediol ether was 1.2:1; the solvent was toluene, and the weight ratio of the toluene to poly[(2-vinyl)-1,2-cyclohexanediol]2-ethyl-2-(hydroxymethyl)-1,3-propanediol ether was 3:1; and the alkaline salt was sodium acetate.

The method for preparing the epoxide comprises the following steps:

(1) The unsaturated cycloaliphatic compound, the organic acid compound, the alkaline salt, and the solvent were mixed, and then cooled to 13° C.;

(2) At a temperature of 20° C. and a pH of 3.7, the hydrogen peroxide solution was added to the above solution dropwise over 2 h, and the reaction was continued for another 4 h;

(3) The resulting solution was left for standing to obtain an underlayer of an organic phase 1, a mixed washing liquid of an inorganic alkaline solution and a reducing salt solution was added thereto and stirred for 20 min at a pH of 11; and the resulting solution was left for standing to obtain an underlayer of an organic phase 2;

(4) The organic phase 2 was first purified by a vacuum distillation at 42° C. for 0.75 h with a vacuum degree of −0.07 MPa, then purified by a two-stage thin film distillation, the temperature of the first-stage thin film distillation was 90° C., the distillation pressure was 200 Pa, the distillation time was 1 h, the temperature of the second-stage thin film distillation was 120° C., the distillation pressure was 20 Pa, and the distillation time was 2 h.

The weight ratio of the mixed washing liquid to the solvent was 1:1.6; the concentration of the inorganic alkaline solution was 30 wt %; the concentration of the reducing salt solution was 10 wt %; the inorganic alkaline was sodium hydroxide; the reducing salt was sodium sulfite, and the content of the reducing salt solution was 44 wt % of the mixed washing liquid.

Example 5

In this example, an epoxide was prepared from raw materials including an unsaturated cycloaliphatic compound containing double bonds, hydrogen peroxide, an organic acid compound, a solvent and an alkaline salt.

The unsaturated cycloaliphatic compound containing double bonds was 4-vinylcyclohexene; the organic acid compound was acetic anhydride with a purity of 98 wt %, and the molar ratio of the acetic anhydride to 4-vinylcyclohexene was 1.2:1; the concentration of the hydrogen peroxide solution was 35 wt %, the molar ratio of the hydrogen peroxide to the 4-vinylcyclohexene was 1.7:1; the solvent was toluene, and the weight ratio of the toluene to 4-vinylcyclohexene was 3:1; and the alkaline salt was sodium acetate.

The method for preparing the epoxide comprises the following steps:

(1) The unsaturated cycloaliphatic compound, the organic acid compound, the alkaline salt, and the solvent were mixed, and then cooled to 13° C.;

(2) At a temperature of 20° C. and a pH of 3.7, the hydrogen peroxide solution was added to the above solution dropwise over 2 h, and the reaction was continued for another 2 h;

(3) The resulting solution was left for standing to obtain an underlayer of an organic phase 1, a mixed washing liquid of an inorganic alkaline solution and a reducing salt solution was added thereto and stirred for 20 min at a pH of 11; and the resulting solution was left for standing to obtain an underlayer of an organic phase 2;

(4) The organic phase 2 was first purified by a vacuum distillation at 42° C. for 0.75 h with a vacuum degree of −0.07 MPa, then purified by a two-stage thin film distillation, the temperature of the first-stage thin film distillation was 30° C., the distillation pressure was 240 Pa, the distillation time was 1 h, the temperature of the second-stage thin film distillation was 75° C., the distillation pressure was 30 Pa, and the distillation time was 0.5 h.

The weight ratio of the mixed washing liquid to the solvent was 1:2.7; the concentration of the inorganic alkaline solution was 30 wt %; the concentration of the reducing salt solution was 10 wt %; the inorganic alkaline was sodium hydroxide; the reducing salt was sodium sulfite, and the content of the reducing salt solution was 45 wt % of the mixed washing liquid.

Example 6

In this example, an epoxide is provided, and the specific implementation thereof is the same as that of Example 4.

The specific implementation of the method for synthesizing the epoxide is the same as that of Example 4, except that after obtaining the organic phase 2 in step (3), it is washed with an aqueous solution to obtain an underlayer of an organic phase 3; the weight ratio of the aqueous solution to the solvent is 1:3; the total amount of the small-molecular amines and trehalose accounts for 20 wt % of the aqueous solution; and the weight ratio of the small-molecular amines to the trehalose is 4:1.

Example 7

In this example, an epoxide is provided, and the specific implementation thereof is the same as that of Example 6.

The specific implementation of the method for synthesizing the epoxide is the same as that of Example 6, except that the small-molecular amine is 3-methylenecyclobutylamine.

Example 8

In this example, an epoxide is provided, and the specific implementation thereof is the same as that of Example 6.

The specific implementation of the method for synthesizing the epoxide is the same as that of Example 6, except that the aqueous solution contains 20 wt % trehalose.

Example 9

In this example, an epoxide is provided, and the specific implementation thereof is the same as that of Example 6.

The specific implementation of the method for synthesizing the epoxide is the same as that of Example 6, except that the aqueous solution contains 20 wt % small-molecular amine.

Example 10

In this example, an epoxide is provided, and the specific implementation thereof is the same as that of Example 4.

The specific implementation of the method for synthesizing the epoxide is the same as that of Example 4, except that the weight ratio of the mixed washing liquid to the solvent is 1:1.

Example 11

In this example, an epoxide is provided, and the specific implementation thereof is the same as that of Example 4.

The specific implementation of the method for synthesizing the epoxide is the same as that of Example 4, except that the reducing salt solution accounts for 55 wt % of the mixed washing liquid.

Example 12

In this example, an epoxide is provided, and the specific implementation thereof is the same as that of Example 4.

The specific implementation of the method for synthesizing the epoxide is the same as that of Example 4, except that the time for the dropwise addition of hydrogen peroxide solution is 10 min, but based on safety considerations, it does not have operability.

Example 13

In this example, an epoxide is provided, and the specific implementation thereof is the same as that of Example 4.

The specific implementation of the method for synthesizing the epoxide is the same as that of Example 4, except that the time for the dropwise addition of hydrogen peroxide solution is 5 h.

Example 14

In this example, an epoxide is provided, the specific implementation thereof is the same as that of Example 4, except that the molar ratio of the organic acid compound to the unsaturated cycloaliphatic compound containing double bonds is 5:1.

The specific implementation of the method for synthesizing the epoxide is the same as that of Example 4.

Example 15

In this example, an epoxide is provided, the specific implementation thereof is the same as that of Example 4, except that the molar ratio of the organic acid compound to the unsaturated cycloaliphatic compound containing double bonds is 1:5.

The specific implementation of the method for synthesizing the epoxide is the same as that of Example 4.

Example 16

In this example, an epoxide is provided, the specific implementation thereof is the same as that of Example 4, except that the molar ratio of the hydrogen peroxide to the double bonds in the unsaturated cycloaliphatic compound is 7:1.

The specific implementation of the method for synthesizing the epoxide is the same as that of Example 4.

Example 17

In this example, an epoxide is provided, and the specific implementation thereof is the same as that of Example 4.

The specific implementation of the method for synthesizing the epoxide is the same as that of Example 4, except that in step (4), it is first purified under reduced pressure, the vacuum degree is −0.07 MPa, the temperature is 42° C., and the time is 0.75 h; and then purified by a one-stage thin film distillation, the temperature is 120° C., the pressure is 85 Pa, and the time is 14 h.

Example 18

In this example, an epoxide is provided, and the specific implementation thereof is the same as that of Example 4.

The specific implementation of the method for synthesizing the epoxide is the same as that of Example 4, except that the pressure of the second-stage thin film distillation is 200 Pa.

Example 19

In this example, an epoxide is provided, and the specific implementation thereof is the same as that of Example 4.

The specific implementation of the method for synthesizing the epoxide is the same as that of Example 4, except that the organic phase 1 is first washed with an inorganic alkaline solution, and then washed with a reducing salt solution.

Performance Evaluation

1. Epoxy equivalent test: The epoxy equivalents of the epoxides finally obtained in Examples 1-11 and 13-19 were tested according to GB/T 4612-2008, and the test results are shown in Table 1.

2. Solvent content test: The solvent content of the final synthesized epoxides in Examples 1-11 and 13-19 was tested by gas chromatography; the solvent content of the epoxides after the first-stage thin film distillation in Examples 1-5 was tested by gas chromatography, and the test results are shown in Table 1.

3. Yield test: The yields of the final synthesized epoxides in Examples 1-11 and 13-19 were tested according to the mass yield, which refers to the percentage of the mass of the product actually obtained to the mass of the raw materials added to the reactor, and the test results are shown in Table 1.

4. Chroma test: The chroma of the final synthesized epoxides in Examples 1-11 and 13-19 was tested according to GB/T22295-2008 Standard Test Method for Color of Transparent Liquids, Part 1: Visual Method. The test results are shown in Table 1.

5. Halogen content test: The total chlorine content in the epoxides synthesized in Examples 1-5, 10, 11 and 17 was tested by ion chromatography, and the test results are shown in Table 2.

TABLE 1

Performance test results of the epoxides finally obtained in Examples 1-11 and 13-19

| | | solvent content (%) | | | |
|---|---|---|---|---|---|
| examples | epoxy equivalent (g/mol) | after the first-stage thin film distillation | after the first-stage thin film distillation | yield (%) | chroma |
| Example 1 | 204 | 1.51 | 0.04 | 102.0 | 20 |
| Example 2 | 201 | 1.48 | 0.05 | 102.0 | 20 |
| Example 3 | 163 | 2.25 | 0.07 | 98.0 | 40 |
| Example 4 | 180 | 2.53 | 0.08 | 105.0 | 25 |
| Example 5 | / | 1.45 | 0.02 | 95.0 | 7 |
| Example 6 | 163 | / | 0.07 | 109.0 | 10 |
| Example 7 | 184 | / | 0.20 | 100.2 | 40 |
| Example 8 | 165 | / | 0.16 | 99.5 | 20 |
| Example 9 | 168 | / | 0.17 | 99.8 | 15 |
| Example 10 | 188 | / | 0.21 | 99.6 | 40 |
| Example 11 | 186 | / | 0.19 | 101.2 | 40 |
| Example 13 | 188 | / | 0.16 | 94.5 | 40 |
| Example 14 | 190 | / | 0.15 | 95.8 | 35 |
| Example 15 | 480 | / | 0.15 | 90.6 | 120 |
| Example 16 | 260 | / | 0.16 | 97.0 | 60 |
| Example 17 | 185 | 1.00 | / | 91.6 | 100 |
| Example 18 | 190 | / | 0.52 | 104.6 | 35 |
| Example 19 | 181 | / | 0.14 | 103.3 | 35 |

TABLE 2

Total chlorine content in the epoxides finally obtained in Examples 1-5, 10, 11 and 17

| examples | total chlorine content (ppm) |
|---|---|
| Example 1 | 120 |
| Example 2 | 115 |
| Example 3 | 150 |
| Example 4 | 145 |
| Example 5 | 60 |
| Example 10 | 160 |
| Example 11 | 153 |
| Example 17 | 152 |

As can be seen from the test results in Tables 1 and 2, the epoxides provided by the present disclosure have a high yield, a low solvent content, low chroma, a low chlorine content, and a low preparation cost, which are suitable for large-scale industrial production.

The foregoing examples are illustrative only and serve to explain some of the features of the methods described herein. The appended claims are intended to claim the broadest conceivable scope and the embodiments presented herein are merely illustrative of selected implementations according to a combination of all possible embodiments. Accordingly, it is the applicant's intention that the appended claims not be limited by the selection of examples that characterize the disclosure. Some numerical ranges used in the claims also include sub-ranges within them, and variations within these ranges should also be construed, where possible, to be covered by the appended claims.

What is claimed is:

1. A method for preparing an epoxide, comprising the steps of:
   mixing an unsaturated cycloaliphatic compound containing a double bond, an alkaline salt, and a solvent, and then cooling;
   adding an organic acid compound thereto;
   dropwise adding a hydrogen peroxide solution thereto to obtain a mixture;
   standing the mixture for layering to obtain a lower organic phase 1;
   washing the lower organic phase 1 with a mixed washing liquid of an inorganic alkaline solution and a reducing salt solution to obtain a mixed solution;
   standing the mixed solution for layering to obtain a lower organic phase 2; and
   purifying the lower organic phase 2 to obtain the epoxide, wherein the organic phase 2 is further washed with an aqueous solution containing:
   a small-molecule amine and trehalose, a total amount of the small-molecular amine and trehalose accounts for 15-30 wt % of the aqueous solution, and a weight ratio of the small-molecular amine to trehalose is (3-5):1.

2. The method for preparing the epoxide according to claim 1, wherein a weight ratio of the mixed washing liquid to the solvent is 1:(2.5-3.5).

3. The method for preparing the epoxide according to claim 1, wherein a time for dropwise adding the hydrogen peroxide solution is 1-3 h.

4. The method for preparing the epoxide according to claim 1, wherein:
   the inorganic alkaline in the inorganic alkaline solution is selected from the group consisting of: sodium hydroxide, potassium hydroxide, sodium carbonate, potassium carbonate, sodium bicarbonate, potassium hydroxide and ammonium hydroxide, and
   a concentration of the inorganic alkaline solution is 20-40 wt %.

5. The method for preparing the epoxide according to claim 1, wherein:
   the reducing salt in the reducing salt solution is selected from the group consisting of: sodium sulfite, ferrous chloride, sodium thiosulfate and ferrous sulfate, and
   a concentration of the reducing salt solution is 10-20 wt %.

6. The method for preparing the epoxide according to claim 1, wherein the reducing salt solution accounts for 40-45 wt % of the mixed washing liquid.

7. The method for preparing the epoxide according to claim 1, wherein a weight ratio of the aqueous solution to the solvent is 1:(2.5-3.5).

8. The method for preparing the epoxide according to claim 1, wherein the purifying is performed through a vacuum distillation and a two-stage thin film distillation in sequence.

* * * * *